United States Patent [19]

Ernst

[11] Patent Number: 4,859,801

[45] Date of Patent: Aug. 22, 1989

[54] SYNTHESIS OF MIXTURES OF BUTANEDIOLS

[75] Inventor: Richard E. Ernst, Kennett Square, Pa.

[73] Assignee: E. I. Du Pont de Nemours and Company, Wilmington, Del.

[21] Appl. No.: 199,192

[22] Filed: May 26, 1988

[51] Int. Cl.$^4$ .................... C07C 29/36; C07C 29/00; C07C 41/01
[52] U.S. Cl. .................... 568/617; 568/865; 568/862; 568/866; 549/509
[58] Field of Search ............... 568/617, 865, 862, 866; 549/509

[56] References Cited

U.S. PATENT DOCUMENTS

| | | | |
|---|---|---|---|
| 3,358,042 | 12/1967 | Dunlop et al. | 568/617 |
| 4,476,332 | 10/1984 | Nelepa | 568/865 |
| 4,590,285 | 5/1986 | Ernst | 549/509 |
| 4,590,312 | 5/1986 | Ernst | 549/509 |

Primary Examiner—Howard T. Mars
Attorney, Agent, or Firm—Charles E. Feeny

[57] ABSTRACT

Process for preparing 2-alkyl-1,4-butanediols and mixtures with 1,4-butanediol which comprises bringing together, at an initial alkaline pH, and at a temperature and pressure suitable for reaction, 2,3-dihydrofuran, hydrogen, an unsubstituted aliphatic aldehyde, especially formaldehyde, and a hydrogenation catalyst. Also processes for preparing mixtures of tetrahydrofuran and 3-alkyltetrahydrofuran from the diol mixtures, and copolymers from the tetrahydrofuran mixtures.

18 Claims, No Drawings

SYNTHESIS OF MIXTURES OF BUTANEDIOLS

FIELD OF THE INVENTION

This invention relates to the synthesis of 2-alkyl-1,4-butanediols from 2,3-dihydrofuran.

BACKGROUND OF THE INVENTION

The 2-alkyl-1,4-butanediols, especially 2-methyl-1,4-butanediol, have a variety of uses. For example, they can be cyclized to the corresponding 3-alkyltetrahydrofurans. Amongst other uses, 3-alkyltetrahydrofurans can be copolymerized with tetrahydrofuran to form polyether glycols, and those glycols can be used in preparing polyurethane elastomers. In the past, 2-alkyl-1,4-butanediols have been prepared by a variety of techniques. For example, they have been prepared by the reduction of itaconic acid. They have also been prepared by the hydroformylation of 1,4-butenediol followed by hydrogenation of the hydroformylation reaction product (believed to be 2-formyl-1,4-butanediol) as described by Copelin in U.S. Pat. No. 3,859,369. In addition, they have been prepared by catalytic hydrogenation of 1,4-butynediol or 1,4-butenediol in the presence of an aldehyde as disclosed in my U.S. Pat. No. 590,312.

While the prior art methods are useful, they are not without their disadvantages. Itaconic acid and the acetylene-based chemicals used in prior art processes are expensive, and there is thus a need for a process which can be operated at a lower cost. In some of the prior art processes, production of 2-alkyl-1,4-butanediols is accompanied by the production of 1,4-butanediol. Those prior art methods yield a greater quantity of 1,4-butanediol than the 2-alkyl-1,4-butanediols. For example, the process disclosed and claimed in my U.S. Pat. No. 4,590,312 gives a diol mixture having a maximum 2-alkyl-1,4-butanediol content of 15 percent by weight. While that may at times be the desired result, at other times it is desirable to prepare mixtures of 2-alkyl-1,4-butanediols and 1,4-butanediol which contain more of the former than the latter.

BRIEF SUMMARY OF THE INVENTION

The process of this invention overcomes the disadvantages of the prior art. It relates to a process for the synthesis of 2-alkyl-1,4-butanediols by reacting 2,3-dihydrofuran with a mixture of an aldehyde and hydrogen in the presence of a catalyst. It relates also to processes for the preparation of 3-alkyltetrahydrofuran and polymers therefrom.

DETAILED DESCRIPTION OF THE INVENTION

The diol synthesis process of this invention can be carried out by bringing together, at an initial alkaline pH, and at a temperature and pressure suitable for reaction, a mixture of 2,3-dihydrofuran, hydrogen, an appropriate unsubstituted aliphatic aldehyde, and a hydrogenation catalyst. The diol synthesis process of the present invention is not limited by any particular theory of operation; however, it is believed that the process proceeds according to the following equations:

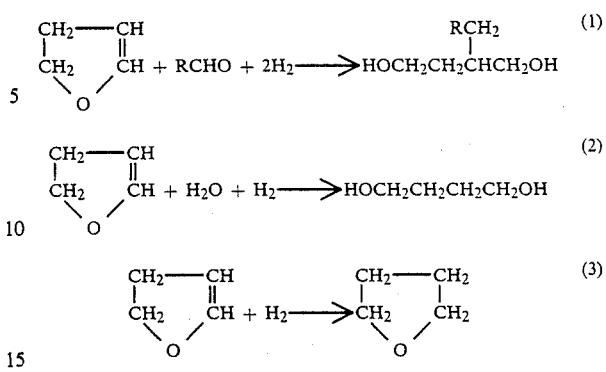

wherein R is hydrogen or an alkyl radical of 1-4 carbon atoms.

While it appears that reductive alkylation proceeds according to Equation 1, part of the 2,3-dihydrofuran is converted to a mixture of 1,4-butanediol and tetrahydrofuran in accordance with Equations 2 and 3.

The product of the diol synthesis process of this invention is a mixture, the organic portion of which is composed predominately of a 2-alkyl-1,4-butanediol, 1,4-butanediol and tetrahydrofuran together with small amounts of low molecular weight alcohols and unidentified high boilers. One of the advantages of the process of this invention is its capacity to provide a diol product mixture having a high 2-alkyl-1,4-butane-diol content. For example, products having a diol content made up of 81 percent by weight of 2-alkyl-1,4-butanediol and 19 percent by weight of 1,4-butanediol have been prepared in accordance with this invention. On the other hand, one of the other advantages of the process of this invention is its flexibility. Thus one can prepare a diol product mixture which contains less 2-alkyl-1,4-butanediol than 1,4-butanediol, either by using less of the aldehyde or less of the base used to provide the alkaline pH under which the process is run.

The components of the mixture of 2-alkyl-1,4-butanediol, 1,4-butanediol and tetrahydrofuran, can be separated from one another by conventional procedures. On the other hand, it is sometimes desirable to keep the mixture intact, for the diols can be cyclized in one step to give a mixture of tetrahydrofuran and a 3-alkyltetrahydrofuran. In addition, a copolymer can be prepared directly from the resulting mixture of tetrahydrofuran and 3-alkyltetrahydrofuran by adding to the mixture of tetrahydrofurans a polymerization catalyst under conditions effective for copolymerization.

The diol synthesis process of this invention may be run either in batch or continuous mode. In either mode, suitable hydrogenation catalysts such as platinum, Raney nickel or cobalt may be used. The preferred catalyst for the preparation of the mixture of diols of this invention is Raney nickel. It can be in the form of a finely divided slurry catalyst (from which most of the aluminum has been removed) for use in a slurry reactor, or in granular form (from which about 25% by weight of the aluminum has been removed) for use in a fixed bed reactor.

The 2,3-dihydrofuran used as the starting material can be prepared by a variety of methods and may be, for example, that obtained by the partial hydrogenation of furan according to the process disclosed by Nowack et al. in U.S. Pat. No. 3,828,077. The unsubstituted aliphatic aldehyde is ordinarily added to the reaction mass as an aqueous solution. Formaldehyde is the preferred aldehyde for use in the process of this invention. Enough is used to provide a 2,3-dihydrofuran: unsubstituted aliphatic aldehyde weight ratio of between about 1:1 to 200:1, preferably between about 2:1 to 25:1.

The pH of the combined reaction mass before contact with hydrogen ( i.e. the initial pH ) is adjusted to the range between about 8 and 14, preferably between about 10 and 12. The reaction can be carried out in the batch mode in a pressure vessel with some provision for agitation. A shaker tube is convenient. The mass is subjected to hydrogen at about 6,895 to 55,160 kPa (gauge), preferably at about 34,475 kPa, for about 30 to 200 minutes, preferably about 100 to 200 minutes, at temperatures in the range between about 100 and 200 minutes, preferably at about 140° and 180° C. The process of this invention can also be run in the continuous mode in a column reactor of appropriate dimensions using basically the same conditions and proportions of reactants as described above. The catalyst should preferably be granular. The hydrogen can be fed either co-current or countercurrent to the other reactants and the temperature can be controlled by recycling the reaction mass. That type of continuous mode operation is described in more detail in my U.S. Pat. No. 4,590,285, the contents of which are incorporated herein by reference.

In another embodiment of the present invention, the diols in the mixture produced by the process of this invention may be catalytically cyclized to a mixture of the corresponding 3-alkyltetrahydrofuran and tetrahydrofuran, using sulfuric acid as the catalyst, according to the process disclosed by Coates et al. in U.S. Pat. No. 3,726,905. In yet another embodiment of the present invention, the resulting mixture of tetrahydrofurans is copolymerized in the presence of a fluosulfonic acid catalyst to form a tetrahydrofuran/3-alkyltetrahydrofuran copolymer in accordance with the process disclosed by Dunlap et al. in U.S. Pat. No. 3,358,042. The resulting copolymer can then be used to prepare a polyurethane in accordance with the method disclosed by Pechold in U.S. Pat. No. 4,120,850. (The contents of each of the foregoing Coates et al., Dunlap et al. and Pechold patents are incorporated herein by reference.)

The following examples further illustrate the present invention. Unless indicated otherwise, all parts, ratios and percentages are by weight and all temperatures are in degrees Celsius.

EXAMPLE 1

Ten parts of 2,3-dihydrofuran, 30 parts of water, 4.3 parts of 37% formaldehyde, 0.53 parts of 30% sodium hydroxide and 5 parts of Raney nickel from which most of the aluminum had been removed, were charged to a high pressure shaker tube and reacted with hydrogen for 2 hours at 150° at 27,576 kPa hydrogen pressure. The organic portion of the resulting product consisted of 29% 2-methyl-1,4-butanediol, 21% 1,4-butanediol, 40% tetrahydrofuran, 4% methanol and 6% unidentified high boilers.

EXAMPLE 2

Twenty parts of 2,3-dihydrofuran, 16 parts of water, 10.8 parts of 37% formaldehyde, 0.53 part of 30% sodium hydroxide, and 5 parts of Raney nickel from which most of the aluminum had been removed, were charged to a high pressure shaker tube and reacted for 2 hours at 150° at 27,576 kPa hydrogen pressure. The organic portion of the resulting product contained 32% 2-methyl-1,4-butanediol, 15% 1,4-butanediol, 31% tetrahydrofuran and 3% methanol.

EXAMPLE 3

Twenty parts of 2,3-dihydrofuran, 10 parts of water, 21.6 parts of 37% formaldehyde, 0.53 part of 30% sodium hydroxide, and 5 parts of Raney nickel from which most of the aluminum had been removed, were charged to a high pressure shaker tube and reacted for 2 hours at 150° at 27,576 kPa hydrogen pressure. The organic portion of the resulting product contained 56% 2-methyl-1,4-butanediol, 13% 1,4-butanediol, 13% tetrahydrofuran and 11% methanol.

EXAMPLE 4

Twenty parts of 2,3-dihydrofuran, 20 parts of water, 4.3 parts of 37% formaldehyde, 0.53 part of 30% sodium hydroxide, and 5 parts of Raney nickel from which most of the aluminum had been removed, were charged to a high pressure shaker tube and reacted for 2 hours at 120° at 27,576 kPa hydrogen pressure. The organic portion of the resulting product contained 13.3% 2-methyl-1,4-butanediol, 10.2% 1,4-butanediol, 72% tetrahydrofuran and 1.7% methanol.

EXAMPLE 5

The reactor used for this experiment was 1.75 inches in diameter and 30 inches high. It was charged with 1000 parts of Raney nickel (8–12 mesh) (activated by removing 25% of the aluminum with NaOH). To this reactor were fed two liquid feed streams, each at 5 cc/min, the first was 2,3-dihydrofuran and the second an aqueous mixture containing 0.4% NaOH and 16% formaldehyde. This was fed concurrently through the reactor with hydrogen at a pressure of 25,576 kPa and a temperature of 150°. A gas chromatographic scan of the product showed that the organic fraction contained 30% 2-methyl-1,4-butanediol, 14% 1,4-butanediol, 25% methanol and 12% tetrahydrofuran.

EXAMPLE 6

A sample of the mixed diols from Example 5 was stripped of water and low boilers by heating to 130°. To this concentrated diol mixture was added 6% of conc. sulfuric acid, and the resulting mixture was heated to 140°, distilling off water and tetrahydrofurans, until about half of the charge was converted. The organic fraction of the stripped product contained 75% 3-methyltetrahydrofuran and 22% tetrahydrofuran.

I claim:
1. A process for the preparation of 2-alkyl-1,4-butanediols, which comprises bringing together, at an initial alkaline pH, and at a temperature and pressure effective for reaction, a mixture of:
   (a) 2,3-dihydrofuran,
   (b) hydrogen,
   (c) an unsubstituted aliphatic aldehyde, and
   (d) a hydrogenation catalyst.
2. A process for preparing a 2-alkyl-1,4-butanediol, comprising
   (a) bringing together at an initial pH in the range between about 8 and 14 and a temperature and pressure effective for reaction:
   (a) hydrogen,
   (b) a hydrogenation catalyst,
   (c) 2,3-dihydrofuran,
   (d) an aldehyde of the structure

R—CHO wherein R is hydrogen or an alkyl radical of containing 1 to 4 carbon atoms,
  in a 2,3-dihydrofuran:aldehyde ratio in the range between about 1:1 to 200:1, and
(b) then separating the resulting 2-alkylbutanediol from the reaction mass.

3. The process of claim 2 wherein said aldehyde is formaldehyde.

4. The method of claim 3 wherein said weight ratio is between about 2:1 and 25:1.

5. The method of claim 4 wherein said pH is in the range between about 10 and 12.

6. A process for the preparation of a mixture of 1,4-butanediol and a 2-alkyl-1,4-butanediol which comprises bringing together, at an initial alkaline pH, and at a temperature and pressure effective for reaction, a mixture of:
(a) hydrogen,
(b) a hydrogenation catalyst,
(c) 2,3-dihydrofuran, and
(d) an unsubstituted aliphatic aldehyde.

7. A process for preparing a mixture of 1,4-butanediol and a 2-alkyl-1,4-butanediol comprising bringing together at an initial pH in the range between about 8 and 14, and a temperature and pressure effective for reaction:
(a) hydrogen,
(b) a hydrogenation catalyst,
(c) 2,3-dihydrofuran,
(d) an aldehyde of the structure

R—CHO wherein R is hydrogen or an alkyl radical of containing 1 to 4 carbon atoms, in a 2,3-dihydrofuran:aldehyde ratio in the range between about 1:1 to 200:1.

8. The process of claim 7 wherein said aldehyde is formaldehyde.

9. The process of claim 8 wherein said weight ratio is between about 2:1 and 25:1.

10. The process of claim 9 wherein said pH is in the range between about 10 and 12.

11. In a process for preparing a mixture of tetrahydrofuran and 3-alkyltetrahydrofuran by cyclizing diols, the improvement comprising using as the diol starting material the mixture of 1,4-butanediol and 2-alkyl-1,4-butanediol prepared in accordance with the process of claim 7.

12. In a process for preparing a mixture of tetrahydrofuran and 3-methyltetrahydrofuran by cyclizing diols, the improvement comprising using as the diol starting material the mixture of 1,4-butanediol and 2-methyl-1,4-butanediol prepared in accordance with the process of claim 8.

13. In a process for preparing a mixture of tetrahydrofuran and 3-methyltetrahydrofuran by cyclizing diols, the improvement comprising using as the diol starting material the mixture of 1,4-butanediol and 2-methyl-1,4-butanediol prepared in accordance with the process of claim 9.

14. In a process for preparing a mixture of tetrahydrofuran and 3-methyltetrahydrofuran by cyclizing diols, the improvement comprising using as the diol starting material the mixture of 1,4-butanediol and 2-methyl-1,4-butanediol prepared in accordance with the process of claim 10.

15. In a process for preparing a copolymer from a mixture of tetrahydrofuran and 3-alkyltetrahydrofuran, the improvement comprising adding a polymerization catalyst to the mixture of tetrahydrofuran and 3-alkyltetrahydrofuran produced in accordance with the process of claim 11 and holding the resulting mixture under conditions effective for polymerization.

16. In a process for preparing a copolymer from a mixture of tetrahydrofuran and 3-methyltetrahydrofuran, the improvement comprising adding a polymerization catalyst to the mixture produced in accordance with the process of claim 12 and holding the resulting mixture under conditions effective for polymerization.

17. In a process for preparing a copolymer from a mixture of tetrahydrofuran and 3-methyltetrahydrofuran, the improvement comprising adding a polymerization catalyst to the mixture produced in accordance with the process of claim 13 and holding the resulting mixture under conditions effective for polymerization.

18. In a process for preparing a copolymer from a mixture of tetrahydrofuran and 3-methyltetrahydrofuran, the improvement comprising adding a polymerization catalyst to the mixture produced in accordance with the process of claim 14 and holding the resulting mixture under conditions effective for polymerization.

* * * * *